United States Patent
Dannecker et al.

(10) Patent No.: US 6,399,051 B2
(45) Date of Patent: Jun. 4, 2002

(54) METHOD AND AGENTS FOR PERMANENTLY STYLING HAIR, WITH A BASE CONSISTING OF N,N-DISUBSTITUTED MERCAPTOACETAMIDES

(75) Inventors: Beate Dannecker, Darmstadt; Guenther Lang, Reinheim; Wolfgang Hanefeld, Marburg/Lahn; Heiko Walther, Gross-Umstadt, all of (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/269,901

(22) PCT Filed: Jul. 25, 1998

(86) PCT No.: PCT/EP98/04678

§ 371 (c)(1),
(2), (4) Date: Jun. 8, 1999

(87) PCT Pub. No.: WO99/07330

PCT Pub. Date: Feb. 18, 1999

(30) Foreign Application Priority Data

Aug. 6, 1997 (DE) .......................... 197 33 952

(51) Int. Cl.$^7$ .................................. A61K 7/09
(52) U.S. Cl. ................ 424/70.5; 424/47; 8/127.51; 132/204; 510/126; 564/224
(58) Field of Search ............... 564/224; 424/70.5, 424/47; 510/126; 132/204; 8/127.51

(56) References Cited

U.S. PATENT DOCUMENTS

| 2,714,119 A | 8/1955 | Crounse et al. |
| 4,220,602 A | 9/1980 | Kalopissis et al. |

FOREIGN PATENT DOCUMENTS

| DE | 948 186 | 8/1956 |
| DE | 972 424 | 7/1959 |
| DE | 196 18 445 A1 | 11/1997 |
| EP | 0 455 457 A2 | 11/1991 |
| EP | 0 514 282 A1 | 11/1992 |
| WO | WO 91/10421 | 7/1991 |
| WO | WO 95/31960 | 11/1995 |
| WO | WO 98/30197 | 7/1998 |

OTHER PUBLICATIONS

Haefele and Broge: "The Synthesis and Properties of Mercaptans Having Different Degrees . . . ", Proceedings of Scientific Section, No. 32, Dec. 1959, pp. 52–59.

*Primary Examiner*—Shailendra Kumar
(74) *Attorney, Agent, or Firm*—Michael J. Striker

(57) ABSTRACT

The present invention relates to a composition and method for permanently shaping hair, in which an N,N-disubstituted mercaptoacetamide of the formula I:

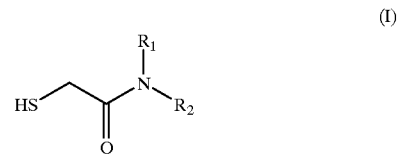

or a salt thereof, wherein $R_1$ and $R_2$ are each independently selected from the group consisting of straight-chain alkyl groups having 1 to 6 carbon atoms, branched-chain alkyl groups having 1 to 6 carbon atoms, monohydroxyalkyl groups having 1 to 6 carbon atoms, polyhydroxyalkyl groups having 1 to 6 carbon atoms and carboxyalkyl groups having 1 to 6 carbon atoms, is employed as keratin reducing agent. A process for making these mercaptoacetamides is also described as well as a novel mercaptoacetamide, N-ethyl-2'-hydroxyethyl-mercaptoacetamide. The mercaptoacetamides provide gentle and uniform shaping of hair in a pH range of 4.5 to 9.5 and do not cause allergic or sensitizing reactions.

4 Claims, No Drawings

METHOD AND AGENTS FOR PERMANENTLY STYLING HAIR, WITH A BASE CONSISTING OF N,N-DISUBSTITUTED MERCAPTOACETAMIDES

This application is a 371 of PCT/EP98/04678, filed Jul. 25, 1998.

BACKGROUND OF THE INVENTION

1. Field of the Invention

The invention relates to agents and methods for permanent hair shaping containing as the keratin-reducing active ingredient an N,N-disubstituted mercaptoacetamide, to a method for producing such mercaptoacetamides and to the new mercaptoacetamide N-ethyl-N-2'-hydroxyethylmercaptoacetamide.

2. Prior Art

As is known, the conventional technique for achieving permanent hair shaping consists of two processing steps: In the first step, the cystine disulfide bonds of hair keratin are broken by the action of an agent containing a reducing substance (shaping agent). Then, the hair is shaped as desired. In a second step, the cystine disulfide bonds are reformed by means of a fixing agent, namely an agent containing an oxidizing substance.

As shown by the pioneering work described in German Patents 948 186 and 972 424, the conventional permanent wave reducing agent is thioglycolic acid used, for example, in the form of its ammonium or monoethanolamine salt. Other common reducing substances are inorganic sulfites, 2-mercaptopropionic acid (thiolactic acid), 3-mercaptopropionic acid, certain mercaptocarboxylic esters, cysteine and derivatives of these compounds.

All these agents, however, have a number of drawbacks. Alkaline preparations based on mercaptocarboxylic acids, in spite of adequate efficacy, cause hair damage manifesting itself, for example, by extensive hair breakage. Frequently, these agents also have an undesirable effect on the scalp. Finally, the unpleasant odor of the reducing agents used requires extensive addition of perfume to the products.

Some of said problems can be solved by use of 2-mercaptopropionic acid (thiolactic acid). Compared to the generally used thioglycolic acid, however, thiolactic acid has a weaker shaping effect.

The mercaptocarboxylic esters which permit hair shaping also at low pH values are unsatisfactory in terms of their skin tolerance and sensitization risk. In place of mercaptocarboxylic esters, mercapto acid amides such as thioglycolic acid amide or alkyl-substituted and hydroxyalkyl-substituted amides can be used. Such compounds are known from patents WO-A-91/10421 and EP-A-0 455 457. Like the carboxylic esters, these compounds have a high shaping potential also at low pH values, but in terms of their sensitizing properties are even worse than the esters.

SUMMARY OF THE INVENTION

The purpose of the invention is therefore to provide an agent and a method for permanent hair shaping which both in the acidic and in the alkaline range (pH=4.0 to 9.0) makes it possible to achieve uniform shaping and which has no sensitizing potential.

Surprisingly, we have now found that the said drawbacks can be avoided by use of N,N-disubstituted mercaptoacetamides having the following formula (I) and that these mercaptoacetamides have a higher shaping potential than thiolactic acid.

Hence, the object of the present invention is an agent for the permanent shaping of hair, characterized in that it contains as the keratin-reducing active ingredient a compound having the general formula

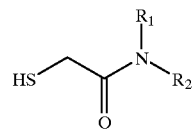

(I)

or a salt thereof, wherein $R_1$ and $R_2$ denote a straight-chain or branched alkyl, monohydroxyalkyl or polyhydroxyalkyl or carboxyalkyl group, each with 1 to 6 carbon atoms.

DETAILED DESCRIPTION OF THE INVENTION

Suitable salts of the mercaptoacetamides of formula (I) are all physiologically tolerated salts, particularly the hydrochloride, sulfate, phosphate, lactate, citrate and acetate.

Preferred are compounds in which $R_1$ and $R_2$ independently of each other denote $CH_3$, $CH_2CH_3$, $CH_2CH_2CH_3$, $CH(CH_3)_2$, $C(CH_3)_3$, $CH_2CH(CH_3)CH_3$, $CH(OH)CH_3$, $CH_2OH$, $CH_2CH_2OH$, $CH_2CH(OH)CH_3$, $CH_2CH_2CH_2OH$, $CH_2CH(OH)CH_2OH$, $CH(CH_3)(CH_2OH)$, $CH(CH_2OH)_2$ or $CH_2COOH$.

Particularly preferred are compounds having the formulas

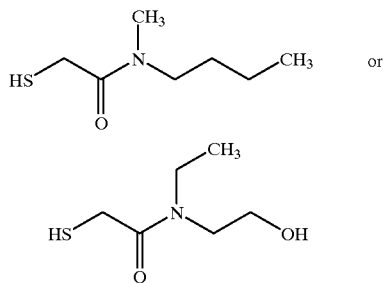

The mercaptoacetamides of formula (I) are present in the ready-for-use hair shaping agent in an amount from 3 to 28 wt % and preferably from 5 to 21 wt %.

In another embodiment of the invention, the mercaptoacetamides of formula (I) can also be used in admixture with other, known thiols, such as thioglycolic acid, thiolactic acid, cysteine, cysteamine and alkyl- or acylcysteamines or sulfites.

The ready-for-use hair shaping agents preferably have a pH of 4.5 to 9.5 a pH, of 6.5 to 8.5 being particularly preferred. Suitable alkalizing and pH-adjusting agents are, in particular, ammonia or sodium hydroxide, but also water-soluble, physiologically tolerated salts of organic and inorganic bases, for example, ammonium hydrogen carbonate.

For marketing purposes, the shaping agents can be packaged as a one-component or a two-component system, the agent possibly being in the form of an aqueous solution or an emulsion or else in thickened, aqueous form, particularly as a cream, gel, foam or paste.

Naturally, the shaping agent can contain all known additives commonly used for such agents, for example, thickeners such as bentonite, fatty acids, starch, polyacrylic acid and derivatives thereof, cellulose derivatives, alginates, vaseline, paraffin oils; wetting agents or emulsifiers from the class of anionic, cationic, amphoteric or nonionic surface-active substances, for example fatty alcohols, fatty alcohol ether sulfates, alkylsulfonates, alkylbenzenesulfonates, quaternary ammonium salts, alkylbetaines, ethoxylated alkylphenols, fatty acid alkanolamides or ethoxylated fatty acid esters; moreover, opacifying agents, such as, for example, polyethylene glycol esters; alcohols, such as, for example, ethanol, propanol, polyols such as, for example, 1,2- or 1,3-propanediol, 1,2-, 1,3- or 1,4-butanediol, 1,2-, 1,3-, 1,4- or 1,5-pentanediol and glycerol; sugars such as, for example, D-glucose; solubilizers, stabilizers, buffers, scented oils, dyes and hair-conditioning and hair-care constituents, such as, for example cationic polymers, lanolin derivatives, cholesterol, pantothenic acid and betaine.

The additive ingredients are used in amounts commonly employed for such purposes. For example the wetting agents and emulsifiers are used at a total concentration of 0.2 to 30 wt %, the alcohols in a total amount of 0.1 to 20 wt %, the opacifying agents, scented oils and dyes in an amount of 0.01 to 1 wt % each, the buffers in a total amount of 0.1 to 10 wt %, sugar, solubilizers, stabilizers and hair-conditioning and hair-care agents in an amount of 0.1 to 5 wt % each, whereas the thickeners and solubilizers can be contained in said agent in a total amount of 0.5 to 20 wt %.

Moreover, for the purpose of enhancing the shaping agent's efficacy, it is possible to add to it swelling agents and penetrants, for example dipropylene glycol monomethyl ether, 2-pyrrolidone or imidazolidin-2-one in an amount of 1 to 30 wt %, and for the purpose of preventing excessively tight hair curling dithio compounds, for example dithioglycolic acid, dithiolactic acid, the disulfides of said compounds or their salts.

By varying the pH, it is possible to provide an agent universally suitable for any hair structure, such an agent optionally being used in conjunction with heat. The agent brings about elastic, lasting and uniform shaping from the root to the tip of the hair without inducing allergic or sensitizing reactions.

Moreover, the present invention relates to a method for permanent hair shaping whereby the hair, before and/or after it was brought into the desired shape, is treated with a shaping agent, rinsed with water, treated with an oxidant, rinsed with water, optionally shaped to a wave using water only and then dried, said method being characterized in that the afore-described agent of the invention is used as the shaping agent.

According to a preferred embodiment of the method of the invention, the hair is first washed with a shampoo and then rinsed with water. The towel-dried hair is then divided into individual strands and wrapped onto a curler with a diameter of 5 to 30 millimeters and preferably 5 to 15 millimeters. The hair is then treated with an amount of the described shaping agent of the invention sufficient for hair shaping, preferably with 60 to 120 grams.

After a period of time sufficient for permanent shaping of the hair which, depending on the hair structure, pH, shaping efficacy of the shaping agent and use temperature, lasts from 5 to 30 min (10 to 30 min if no heat is used; 5 to 20 min with heating), the hair is rinsed with water and then post-treated ("fixed") with an oxidant. The post-treatment agent is preferably used in an amount of 80 to 100 grams, depending on hair fullness.

For the oxidizing post-treatment in the wrapped or unwrapped state, any post-treatment agent suitable for such treatment can be used. Examples of oxidants that can be used in such post-treatment agents are potassium and sodium bromate, sodium perborate, urea peroxide and hydrogen peroxide. The concentration of the oxidant varies depending on the application time (as a rule 5 to 15 min) and the application temperature. The oxidant is usually present in the ready-for-use aqueous post-treatment agent at a concentration of 0.5 to 10 wt %. The agent for the oxidizing post-treatment can, of course, also contain other substances, for example wetting agents, care materials such as cationic polymers, weak acids, buffers or peroxide stabilizers, and it can be in the form of an aqueous solution, an emulsion or in thickened form on an aqueous basis, particularly as a cream, gel or paste. In particular, these common additives can be contained in the post-treatment agent in an amount of 0.1 to 10 wt %.

The curlers are then removed. If necessary, the unwrapped hair is subjected to another oxidizing treatment. The hair is then rinsed with water, optionally set to a wave using water only and then dried.

Another object of the invention is a method for making the mercaptoacetamides of formula (I) whereby an appropriate secondary amine is made to react with methyl thioglycolate at a temperature not exceeding 30° C. Said method is described more closely in Preparation Example 1, method A, and Preparation Examples 2, 4 and 5.

Yet another object of the invention is the novel N-ethyl-N-2'-hydroxyethylmercaptoacetamide, obtained by the afore-described method.

The following examples will explain the invention in greater detail without limiting the scope of the invention to these examples.

EXAMPLE 1

Preparation of the Mercaptoacetamides by Method A

Two moles of the appropriate primary amine was charged to a 500-mL three-necked flask. One mole of methyl thioglycolate was then slowly added dropwise with water-bath cooling so that the temperature did not exceed 30° C. The batch was flushed with argon and allowed to agitate until the methyl thioglycolate had quantitatively reacted (check by thin layer chromatography on 5×10 cm Merck DC-aluminum sheets; silica gel 60 F 254).

The mixture was acidified with 36% hydrochloric acid with ice cooling (pH 2–4) and exhaustively extracted with ethyl acetate. The solvent was distilled off under vacuum in a rotary evaporator, the residue was brought to pH 7.0 by addition of sodium hydroxide solution and again extracted by shaking with ethyl acetate. The combined fractions were dried over sodium sulfate and concentrated. The resulting residue was subjected to molecular distillation at 0.01 torr max. to give a virtually pure product. This procedure is of critical significance if it is desired to obtain as pure a product as possible in good yield. Because of their sensitizing properties, impurities consisting of incompletely reacted cleavage products formed by thermolysis or hydrolysis can be avoided only by careful distillation.

Preparation of Mercaptoacetamides by Method B

In a 1-L three-necked flask, one mole of the appropriate primary amine was dissolved in 500 mL of water and cooled to 0° C. in an ice-water bath. To the solution was added 250 mL of 2 N NaOH, and one mole of chloroacetyl chloride was added dropwise so as not to exceed a temperature of 5° C. The batch was allowed to agitate vigorously at room temperature for three hours. To the mixture was then added one mole of potassium methylxanthogenate, and the mixture was allowed to agitate at room temperature for an additional twelve hours. The mixture was then acidified with 36% hydrochloric acid until a yellow oil separated. This oil was isolated and dissolved in a mixture of 500 mL of 25% ammonia and 250 mL of ethanol, and the resulting solution was allowed to agitate 1 hour at room temperature. The ethanol was then distilled off under vacuum in a rotary evaporator, and the residue was extracted with ethyl acetate. The aqueous phase was carefully acidified and once again extracted with ethyl acetate. The solvent was distilled off under vacuum in a rotary evaporator. The residue was then purified by distillation (see method A) or recrystallized from ethyl acetate.

d) Thiol titration: 95.36%;

e) Elemental analysis: $C_4H_8NOS$ (mol. wt. 119.19); Calcd.: C, 40.33; H: 7.56; N: 11.76; S: 26.92. Found: C, 39.61; H: 7.41; N: 11.53; S: 26.58.

f) IR (KBr) 2931 s ($CH_2$); 2542 w (SH); 1644 s (N,N-disubstituted amide).

g) HPLC HPLC gave 98.45 area percent for the compound. (column: C 18 5U, 250 mm×4.6 mm; mobile phase acetonitrile: buffer [4 g $KH_2PO_4$+0.8 g sodium octanesulfonate+2 mL $H_3PO_4$]; flow rate: 0.5 mL/min; wavelength 200 nm; =25:75).

h) pKa 7.92 ($H_2O$);

i) UV max. 210.4 nm (acetonitrile:buffer=25:75);

j) Boiling point 73° C./0.03 torr.

TABLE 1

| Mercaptoacetamide (amine component) | Yield | Elemental Analysis calculated found | | HPLC area % | Boiling point | Standardized Wave Stability | | |
|---|---|---|---|---|---|---|---|---|
| | | | | | | WSN pH = 7 | WSN pH = 8 | WSN pH = 9 |
| 1) N,N-Dimethylmercaptoacetamide (Dimethylamine) | 73% | C: 40,33, N: 11,76, C: 39,61, N: 11,53, | H: 7,56, S: 26,92, H: 7,41, S: 26,58 | 98,45% | 73° C./ 0,03 Torr | 81% | 98% | 98% |
| 2) N,N-Diethylmercaptoacetamide (Diethylamine) | 35% | C: 48,94, N: 9,51, C: 48,40, N: 9,60, | H: 8,90, S: 21,78, H: 8,89, S: 21,83 | 99,19% | 74° C./ 0,1 Torr | 83% | 98% | 106% |
| 3) N-Butyl-N-methylmercaptoacetamide (Butylmethylamine) | 25% | C: 52,14, N: 8,69, C: 51,86, N: 8,85, | H: 9,38, S: 19,88, H: 9,03, S: 19,82 | 99,19% | 88° C./ 0,075 Torr | 63% | 67% | 87% |
| 4) N-Ethyl-N-2'-hydroxyethylmercapto-acetamide (N-ethyl-N-hydroxyethylamine) | 58% | C: 44,15, N: 8,58, C: 44,21, N: 8,37, | H: 8,03, S: 19,64, H: 7,83, S: 19,30 | 98,35% | 108° C./ 0,075 Torr | 78% | 95% | 99% |
| Thiolactic acid for comparison | | | | | | 57% | 50% | 70% |

In material reproduced from the orginal, commas denote decimal points - Translator
WSN = SWS = standardized wave stability - Translator

EXAMPLE 2

Preparation of N,N-Dimethylmercaptoacetamide 225 g (2 moles) of 40% aqueous dimethylamine solution was charged to a 500-mL three-necked flask. Then, 106.24 g of methyl thioglycolate was slowly added dropwise so as not to exceed a temperature of 30° C. The batch was flushed with argon and allowed to agitate 2 days at room temperature.

The mixture was acidified with 36% hydrochloric acid with ice cooling (pH 2–4) and exhaustively extracted with ethyl acetate. The solvent was distilled off under vacuum in a rotary evaporator and the residue was brought to pH 7.0 by addition of sodium hydroxide solution and once again extracted by shaking with ethyl acetate. The combined fractions were dried over sodium sulfate and concentrated. The residue was subjected to molecular distillation at 0.01 torr max. to obtain the pure product. The yield was 87 g (73%).

Analysis:

a) $^1$H-NMR ($CDCL_3$): δ (ppm)=3.34 (s, 2H, HS—$CH_2$—CO); 3.07 (s, 3H, N—$CH_3$); 2.99 (s, 3H, N—$CH_3$); 2.0 (broad, 1H, HS);

b) $^{13}$C-NMR ($CDCL_3$): δ (ppm)=169.42 (—C=O); 37.38 (N—$CH_3$)); 35.68 (N—$CH_3$); 26.00 (HS—$CH_2$);

c) MS (70 e V, El, RT) m/z (%)=($M^+$)=119 (40.06) 86 (14.4), 72 (100), 44 (46.46),

EXAMPLE 3

Preparation of N,N-Diethylmercaptoacetamide

In a 1-L three-necked flask, 73 g (1 mole) of diethylamine was dissolved in 500 mL of water and cooled to 0° C. in an ice-water bath. To the solution was added 250 mL of 2 N NaOH, and then 112 g (1 mole) of chloroacetyl chloride was added dropwise so as not to exceed a temperature of 5° C. The batch was allowed to agitate vigorously for three hours at room temperature. Then, 160.3 g (1 mole) of potassium methylxanthogenate was added to the mixture, and the mixture was allowed to agitate for an additional twelve hours at room temperature. The mixture was acidified with 36% hydrochloric acid until a yellow oil separated. This oil was isolated and dissolved in a mixture of 500 mL of 25% ammonia and 250 mL of ethanol. The resulting mixture was allowed to agitate one hour at room temperature. The ethanol was then distilled off under vacuum in a rotary evaporator, and the residue was extracted by shaking with ethyl acetate. The aqueous phase was acidified with 36% hydrochloric acid with ice cooling (pH 2–4) and exhaustively extracted with ethyl acetate. The solvent was distilled off under vacuum in a rotary evaporator and the residue was brought to pH 7.0 by addition of sodium hydroxide solution and once again extracted with ethyl acetate. The combined fractions were dried over sodium sulfate and concentrated.

The resulting residue was subjected to molecular distillation at 0.01 torr max. to obtain a pure product. The yield was 51.5 g (35%).

Analysis:

a) $^1$H-NMR (CDCL$_3$): δ (ppm)=3.3–3.4 (m+s, 6H, 2×N—CH$_2$+HS—CH$_2$—CO); 2.1 (t, 1H, HS); 1.1–1.2 (2×d, 6H, 2×CH$_3$);

b) $^{13}$C-NMR (CDCL$_3$): δ (ppm)=168.99 (C=O); 42.60 (N—CH$_2$); 40.8 (N—CH$_2$); 26.26 (HS—CH$_2$); 14.47+12.86 (2×CH$_3$);

c) MS (70 e V, EI, RT) m/z (%)=(M$^+$)=147 (22.76); 114 (74.1), 100 (35.41), 86 (4.73), 72 (100), 58 (46.3), 44 (38);

d) Thiol titration: 98.56%;

e) Elemental analysis: C$_6$H$_{13}$NOS (mol. wt. 147.24 g/mole); Calculated: C, 48.94, H, 8.90, N, 9.51, S, 21.78. Found: C, 48.40, H, 8.89, N, 9.60, S, 21.83.

f) IR (KBr) 2975–2935 s (CH$_2$); 2545 w (SH); 1639 s (N,N-disubstituted amide);

g) HPLC HPLC analysis gave 99.18 area percent for the compound. (Column: C 18 5U, 250 mm×4.6 mm, mobile phase acetonitrile: buffer [4 g KH$_2$PO$_4$+0.8 g Na octanesulfonate+2 mL H$_3$PO$_4$] flow rate 0.5 mL/min; wavelength 200 nm; =25:75).

h) pKa 8.361 (H$_2$O);

i) UV max: 227 nm (acetonitrile:buffer=25:75);

j) Boiling point: 74° C./0.1 torr.

EXAMPLE 4

Preparation of N-Butyl-N-Methylmercaptoacetamide 174 g (2 moles) of butylmethylamine was charged to a 500-mL three-necked flask and to it was slowly added dropwise 106.24 g of methyl thioglycolate so as not to exceed a temperature of 30° C. The batch was flushed with argon and allowed to agitate 2 days at room temperature. The mixture was acidified with 36% hydrochloric acid with ice cooling (pH 2–4) and exhaustively extracted with ethyl acetate. The solvent was distilled off under vacuum in a rotary evaporator and the residue was brought to pH 7.0 by addition of sodium hydroxide solution and once again extracted by shaking with ethyl acetate. The combined fractions were dried over sodium sulfate and concentrated. The resulting residue was subjected to molecular distillation at 0.01 torr max. to obtain the pure product. The yield was 40 g (25%).

Analysis:

a) $^1$H-NMR (CDCL$_3$): δ (ppm)=3.34–3.26 (m, 4H, HS—CH$_2$—CO+N—CH$_2$); 3.0–2.91 (2×d, 3H, N—CH$_3$); 2.16 (broad, 1H, HS); 1.55–1.46 (m, 2H, N—CH$_2$—CH$_2$); 1.29–1.27 (m, 2H, CH$_2$—CH$_2$—CH$_2$—CH$_3$); 0.9 (2×t, 3H, CH$_3$);

b) $^{13}$C-NMR (CDCL$_3$): δ (ppm)=169.67+169.56 (—C=O); 50.4+48.17 (N—CH$_2$); 35.7+34.01 (N—CH$_3$)); 30.68+29.25 (N—CH$_2$—CH$_2$—CH$_2$); 26,63+25.99 (HS—CH$_2$); 20.02 (CH$_2$—CH$_3$); 13.88 (CH$_2$—CH$_3$);

c) MS (70 e V, EI, RT) m/z (%)=(M$^+$)=161 (19.29), 128 (28.9), 114 (23.5), 100 (11.23), 86 8 (10.4), 57 (50.5), 44 (100);

d) Thiol titration: 98.48%;

e) Elemental analysis: C$_7$H$_{15}$NOS (mol. wt. 161.26 g/mole); Calculated: C, 52.14, H, 9.38, N, 8.69, S, 19.88. Found: C, 51.86, H, 9.03, N, 8.85, S, 19.82.

f) IR (KBr) 2930–2869 s (CH$_2$); 2547 w (SH); 1643 s (N,N-disubstituted amide);

g) HPLC HPLC analysis gave 99.19 area percent for the compound. (Column: C 18 5U, 250 mm×4.6 mm, mobile phase acetonitrile: buffer [4 g KH$_2$PO$_4$+0.8 g Na octanesulfonate+2 mL H$_3$PO$_4$] flow rate 0.5 mL/min; wavelength 200 nm; =25:75).

h) pKa 7.873 (H$_2$O);

i) UV max: 230.8 nm (acetonitrile:buffer=25:75);

j) Boiling point: 88° C./0.075 torr.

EXAMPLE 5

Preparation of N-Ethyl-N-2'-Hydroxyethylmercaptoacetamide 168 g (2 moles) of N-ethyl-N-2'-hydroxyethylamine was charged to a 500-mL three-necked flask and to it was added slowly and dropwise 106.24 g of methyl thioglycolate so as not to exceed a temperature of 30° C. The batch was flushed with argon and allowed to agitate 2 days at room temperature. The mixture was acidified with 36% hydrochloric acid with ice cooling (pH 2–4) and exhaustively extracted with ethyl acetate. The solvent was distilled off under vacuum in a rotary evaporator and the residue was brought to pH 7.0 by addition of sodium hydroxide solution and once again extracted by shaking with ethyl acetate. The combined fractions were dried over sodium sulfate and concentrated. The resulting residue was subjected to molecular distillation at 0.01 torr max. to obtain the pure product. The yield was 95 g (58%).

Analysis:

a) $^1$H-NMR (CDCL$_3$): δ (ppm)=3.72 (m, 2H, CH$_2$—OH); 3.41 (t, 1H, OH); 3.39–3.3 (m, 6H, HS—CH$_2$—CO+2×N—CH$_2$); 2.14 (t, 1H, HS); 1.22–1.1 (2t, 3H, CH$_3$);

b) $^{13}$C-NMR (CDCL$_3$): δ (ppm)=171.43 (—C=O); 61.63 (CH$_2$—OH); 49.47 (N—CH$_2$—CH$_2$—OH); 44.55 (N—CH$_2$—CH$_3$); 26.01 (HS—CH$_2$); 14.12 (CH$_3$);

c) MS (70 e V, EI, 30° C.) m/z (%)=(M$^+$)=163 (52.22) 132 (31.7), 131 (77.9), 120 (18.99), 112 (16.14) 88 (52.5), 70 (34.22), 58 (100);

d) Thiol titration: 98.03%;

e) Elemental analysis: C$_6$H$_{13}$NO$_2$S (mol. wt. 163.23 g/mole); Calculated: C, 44.15, H, 8.03, N, 8.58, S, 19.64. Found: C, 44.21, H, 7.83, N, 8.37, S, 19.30.

f) IR (KBr) 3407 s (OH); 2974–2849 (CH$_2$); 2545 w (SH); 1625 s (N,N-disubstituted amide);

g) HPLC HPLC analysis gave 98.35 area percent for the compound. (Column: C 18 5U, 250 mm×4.6 mm, mobile phase acetonitrile: buffer [4 g KH$_2$PO$_4$+0.8 g Na octanesulfonate+2 mL H$_3$PO$_4$] flow rate 0.5 mL/min; wavelength 200 nm; =25:75).

h) pKa 7.604 (H$_2$O);

i) UV max: 234.4 m [sic—"nm" is meant—Translator] (acetonitrile:buffer=25:75);

j) Boiling point: 108° C./0.075 torr.

EXAMPLE 6

Comparison of Waving Efficacy

The waving efficacy of 1-mercaptoacetamides was determined with the aid of waving solutions at pH 7, 8 and 9 using glycerol monothioglycolate for comparison. To this end, 16.5 cm-long strands of prebleached and thus damaged counted mid-European hair (about 100 hairs) were wrapped wet onto standardized spiral curlers (inner diameter: 3 millimeters) and after conditioning in a conditioning room (temperature: 20° C.; air humidity 65%) treated with a solution containing 87 mmol of reducing agent/100 g and adjusted to the indicated pH. The quantity of waving solution applied was calculated to conform to a 1:1.2 ratio (1 g of hair: 1.2 mL of waving solution). The solution was allowed to act for 20 min at a temperature of 50° C. The hair was then fixed with a peroxide-containing fixing agent and dried. After unwrapping, the hair was suspended in water for 4 hours (water bath temperature: 40° C.).

Wave stability was calculated by the following expresion:

$$\text{Wave stability, \%} = \frac{l_0 - l_t}{l_0 - l_1}$$

$l_0$ = total length of unshaped, stretched strands (16.5 cm)

$l_t$ = length of unwrapped, suspended strands after 240 minutes $l_1$ = length of shaped, wrapped strands
(for a curler with an inner diameter of 3 mm, this length is 35 mm).

Strands treated with a glycerol monothioglycolate solution adjusted to pH 9 were used as the standard. The standardized wave stability values (SWS) refer to this standard solution (pH 9) for which the wave stability was set at 100%.

Table 1 shows that the wave stabilities for the mercaptoacetamides according to the invention at pH 7, 8 and 9 are higher than those for thiolactic acid.

EXAMPLE 7

| Permanent Shaping Agent for Dyed Hair | |
|---|---|
| 10.5 g | N,N-dimethylmercaptoacetamide |
| 0.4 g | ammonia (25% aqueous solution) for pH adjustment |
| 2.0 g | ammonium hydrogen carbonate |
| 2.0 g | dipropylene glycol monoethyl ether |
| 1.0 g | isooctylphenol, ethoxylated with 10 moles of ethylene oxide |
| 1.0 g | poly(dimethyldiallylammonium chloride) |
| 0.3 g | scented oil |
| 0.1 g | vinylpyrrolidone/styrene copolymer (Antara ® 430, GAF Corp., New York, USA) |
| 84.7 g | water |
| 100.0 g | |

This agent had a pH of 7.3.

Hair previously damaged by dyeing treatments was washed with a shampoo, dried with a towel and wrapped onto curlers 8 mm in diameter. The afore-described hair shaping agent was then uniformly distributed over the wrapped hair. The hair was then covered with a plastic cap and warmed under a hood drier at a temperature of 45° C. for 10 minutes. The cap was then removed. The hair was rinsed with water and then subjected to an oxidizing post-treatment with a 3% aqueous hydrogen peroxide solution. After removal of the culers, the hair was again rinsed with water, set to a wave using water only and then dried.

This treatment resulted in uniform, elastic and permanent shaping of the hair.

EXAMPLE 8

| Permanent Wave Agent for Normal Hair | |
|---|---|
| 15.9 g | N,N-diethylmercaptoacetamide |
| 8.9 g | ammonia (25% aqueous solution) |
| 5.0 g | ammonium hydrogen carbonate |
| 5.0 g | isopropanol |
| 5.0 g | 1,2-propylene glycol |

| -continued | |
|---|---|
| Permanent Wave Agent for Normal Hair | |
| 2.4 g | monoethanolamine |
| 1.5 g | isooctylphenol, ethoxylated with 10 moles of ethylene oxide |
| 0.5 g | poly(dimethyldiallylammonium chloride) |
| 0.5 g | scented oil |
| 0.1 g | vinylpyrrolidone/styrene copolymer (Antara ® 430, GAF Corp; New York, USA) |
| 55.2 g | water |
| 100.0 g | |

This agent had a pH of 8.4.

Normal, not predamaged hair was washed, dried with a towel and wrapped onto curlers 6 mm in diameter. The hair was then uniformly moistened with the afore-described permanent wave agent. After a 15-min treatment period, the hair was thoroughly rinsed and then subjected to an oxidizing post-treatment with 80 g of a 3% aqueous hydrogen peroxide solution. After removal of the curlers, the hair was again rinsed with water, set to a wave using water only and then dried. This hair treatment produced uniform and bouncy curls.

EXAMPLE 9

| Permanent Wave Agent for Normal Hair | |
|---|---|
| 8.8 g | N-ethyl-N-2'-hydroxyethylmercaptoacetamide |
| 8.8 g | N-butyl-N-methylmercaptoacetamide |
| 5.0 g | ammonia (25% aqueous solution) for pH adjustment |
| 5.0 g | ammonium hydrogen carbonate |
| 5.0 g | 1,2-pentanediol |
| 2.0 g | D-glucose |
| 2.4 g | ammonia |
| 1.5 g | isooctylphenol ethoxylated with 10 moles of ethylene oxide |
| 0.5 g | poly(dimethyldiallylammonium chloride) |
| 0.5 g | scented oil |
| 0.1 g | vinylpyrrolidone/styrene copolymer (Antara ® 430, GAF Corp., New York, USA) |
| 60.4 g | water |
| 100.0 g | |

This agent had a pH of 8.3.

Normal, not predamaged hair was washed, dried with a towel and wrapped onto curlers 6 mm in diameter. The hair was then uniformly moistened with the afore-described permanent wave agent. After a 15–25 min treatment period, the hair was thoroughly rinsed and then subjected to an oxidizing post-treatment with 80 g of a 3% aqueous hydrogen peroxide solution. After removal of the curlers, the hair was again rinsed with water, set to a wave with water only and then dried. This hair treatment produced uniform and bouncy curls.

EXAMPLE 10

| Permanent Wave Agent for Normal Hair | |
|---|---|
| 17.5 g | N-ethyl-N-2'-hydroxyethylmercaptoacetamide |
| 8.0 g | ammonia (25% aqueous solution) for pH adjustment |
| 5.0 g | ammonium hydrogen carbonate |
| 5.0 g | 1,2-pentanediol |

-continued

Permanent Wave Agent for Normal Hair

| | | |
|---|---|---|
| 2.4 | g | ammonia |
| 1.5 | g | isooctylphenol ethoxylated with 10 moles of ethylene oxide |
| 0.5 | g | poly(dimethyldiallylammonium chloride) |
| 0.5 | g | scented oil |
| 0.1 | g | vinylpyrrolidone/styrene copolymer (Antara ® 430, GAF Corp., New York, USA) |
| 59.5 | g | water |
| 100.0 | g | |

This agent had a pH of 8.3.

Normal not predamaged hair was washed, dried with towel and wrapped onto curlers 6 mm in diameter. The hair was uniformly moistened with the afore-described permanent wave agent. After a 15–25 min treatment period, the hair was throroughly rinsed and then subjected to an oxidizing post-treatment with 80 g of a 3% aqueius hydrogen peroxide solution. After removal of the curlers, the hair was again rinsed with water, set to a wave using water only and then dried. This hair treatment produced uniform and bouncy curls.

What is claimed is:

1. A composition for permanently shaping hair, said composition having a pH of from 4.5 to 9.5 and comprising
   from 3 to 28 percent by weight of at least one N,N-disubstituted mercaptoacetamide selected from the group consisting of N,N-dimethyl-mercaptoacetamide, N,N-diethylmercaptoacetamide, N-methyl-N-butyl-mercaptoacetamide and N-ethyl-N-2'-hydroxyethylmercaptoacetamide, or a physiologically compatible salt thereof;
   water;
   at least one pH adjusting agent;
   from 0.2 to 30 percent by weight of at least one surface-active substance selected from the group consisting of anionic surfactants, cationic surfactants, amphoteric surfactants and nonionic surfactants;
   from 0.01 to 1 percent by weight of at least one additional ingredient selected from the group consisting of opacifying agents and scented oils; and
   from 0.1 to 10 percent by weight of at least one buffer.

2. A composition for permanently shaping hair, said composition having a pH of from 6.5 to 8.5 and comprising
   from 5 to 21 percent by weight of at least one N,N-disubstituted mercaptoacetamide, or a physiologically-.compatible salt thereof, and wherein said at least one N,N-disubstituted mercaptoacetamide is selected from the group consisting of N-methyl-N-butylmercaptoacetamide and N-ethyl-N-2'-hydroxyethylmercaptoacetamide;
   water;
   at least one pH adjusting agent;
   from 0.2 to 30 percent by weight of at least one surface-active substance selected from the group consisting of anionic surfactants, cationic surfactants, amphoteric surfactants and nonionic surfactants;
   from 0.01 to 1 percent by weight of at least one additional ingredient selected from the group consisting of opacifying agents and scented oils; and
   from 0.1 to 10 percent by weight of at least one buffer.

3. A method of permanently shaping hair without risk of skin sensitization, said method comprising the steps of:

a) applying an amount of an aqueous hair shaping composition to hair that is sufficient for the permanent shaping of the hair, wherein said aqueous hair shaping composition has a pH of from 4.5 to 9.5 and comprises water; at least one pH adjusting agent; from 3 to 28% by weight of at least one N,N-disubstituted mercaptoacetamide selected from the group consisting of N,N-dimethyl-mercaptoacetamide, N,N-diethylmercapto-acetamide, N-methyl-N-butyl-mercaptoacetamide and N-ethyl-N-2'-hydroxyethyl-mercaptoacetamide, or a physiologically compatible salt thereof; from 0.2 to 30 percent by weight of at least one surface-active substance selected from the group consisting of anionic surfactants, cationic surfactants, amphoteric surfactants and nonionic surfactants; from 0.01 to 1 percent by weight of at least one additional ingredient selected from the group consisting of opacifying agents and scented oils and from 0.1 to 10 percent by weight of at least one buffer;

b) putting the hair into a predetermined shape;

c) allowing the aqueous hair shaping composition to act on the hair after the hair has been put in the predetermined shape for a sufficient acting time for the permanent shaping of the hair;

d) after the allowing of step c), rinsing the hair with water;

e) after the rinsing of step d) subjecting the hair to an oxidizing post-treatment; and f) after the post-treatment of step e) rinsing the hair with water and subsequently drying the hair.

4. A method of permanently shaping hair without risk of skin sensitization, said method comprising the steps of:

a) applying an amount of an aqueous hair shaping composition to hair that is sufficient for the permanent shaping of the hair, wherein said aqueous hair shaping composition has a pH of from 6.5 to 8.5 and comprises water; at least one pH adjusting agent; from 5 to 21 percent by weight of at least one N,N-disubstituted mercaptoacetamide selected from the group consisting of N,N-dimethylmercaptoacetamide, N,N-diethylmercaptoacetamide, N-methyl-N-butyl-mercaptoacetamide and N-ethyl-N-2'-hydroxyethylmercaptoacetamide, or a physiologically compatible salt thereof; from 0.2 to 30 percent by weight of at least one surface-active substance selected from the group consisting of anionic surfactants, cationic surfactants, amphoteric surfactants and nonionic surfactants; from 0.01 to 1 percent by weight of at least one additional ingredient selected from the group consisting of opacifying agents and scented oils and from 0.1 to 10 percent by weight of at least one buffer;

b) putting the hair into a predetermined shape;

c) allowing the aqueous hair shaping composition to act on the hair after the hair has been put in the predetermined shape for a sufficient acting time for the permanent shaping of the hair;

d) after the allowing of step c), rinsing the hair with water;

e) after the rinsing of step d) subjecting the hair to an oxidizing post-treatment; and f) after the post-treatment of step e) rinsing the hair with water and subsequently drying the hair.

* * * * *